US011123477B2

(12) United States Patent
Eliasson

(10) Patent No.: US 11,123,477 B2
(45) Date of Patent: Sep. 21, 2021

(54) MOTORIZED IRRIGATION SYSTEM WITH IMPROVED FLOW CONTROL

(71) Applicant: DENTSPLY IH AB, Mölndal (SE)

(72) Inventor: Göran Eliasson, Stenungsund (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

(21) Appl. No.: 15/705,710

(22) Filed: Sep. 15, 2017

(65) Prior Publication Data
US 2018/0078700 A1 Mar. 22, 2018

(30) Foreign Application Priority Data

Sep. 16, 2016 (EP) ..................................... 16189171

(51) Int. Cl.
*A61M 39/28* (2006.01)
*A61M 3/02* (2006.01)

(52) U.S. Cl.
CPC .......... *A61M 3/0258* (2013.01); *A61M 3/022* (2014.02); *A61M 3/0237* (2013.01);
(Continued)

(58) Field of Classification Search
CPC .. A61M 3/0258; A61M 3/022; A61M 3/0237; A61M 3/0279; A61M 3/0295; A61M 39/28
(Continued)

(56) References Cited

U.S. PATENT DOCUMENTS 3,737,676 A * 6/1973 Fletcher ................. H03B 19/00
327/117
4,530,463 A * 7/1985 Hiniker .................... B05B 9/06
239/155
(Continued)

FOREIGN PATENT DOCUMENTS

CN 101848741 9/2010
CN 102137689 7/2011
(Continued)

OTHER PUBLICATIONS

European Search Report for European Patent Application No. 16189171.8, dated Mar. 27, 2017 (7 pages).
(Continued)

*Primary Examiner* — Nathan R Price
*Assistant Examiner* — Mark A Igel
(74) *Attorney, Agent, or Firm* — Perkins Coie LLP

(57) ABSTRACT

Disclosed are irrigation systems and methods, which can be used for rectal/anal irrigation. One example system includes a reservoir for an irrigating liquid, a probe for arrangement in a user, tubing providing fluid communication between the reservoir and probe, and an electrical pump for indirectly pumping irrigation liquid from the reservoir to the probe through said tubing. The electrical pump is controllable to assume a plurality of predetermined flow rates. The system includes an electrically operable valve to continuously control a degree of openness of the tubing, a flow sensor to measure an actual flow rate of the irrigation liquid in the probe, and a controller to obtain a desired flow rate, and control the flow rate of the electric pump to one of the plurality of flow rates exceeding the desired flow rate, and to continuously regulate the electrically operable valve based on the measured actual flow rate.

12 Claims, 8 Drawing Sheets

(52) U.S. Cl.
CPC ........ *A61M 3/0279* (2013.01); *A61M 3/0295* (2013.01); *A61M 39/28* (2013.01); A61M 2205/07 (2013.01); A61M 2205/3334 (2013.01); A61M 2205/50 (2013.01); A61M 2210/1064 (2013.01); A61M 2210/1067 (2013.01)

(58) Field of Classification Search
USPC .................................. 128/DIG. 12, DIG. 13
See application file for complete search history.

(56) References Cited

U.S. PATENT DOCUMENTS

| | | | | |
|---|---|---|---|---|
| 5,830,176 | A * | 11/1998 | Mackool | A61M 1/0058 604/22 |
| 6,106,506 | A * | 8/2000 | Abell | A61M 3/0208 604/275 |
| 6,228,048 | B1 * | 5/2001 | Robbins | A61M 3/0241 604/27 |
| 6,689,091 | B2 * | 2/2004 | Bui | A61M 5/172 604/67 |
| 6,768,452 | B2 * | 7/2004 | Gilkes | G01S 19/256 342/352 |
| 7,914,505 | B2 * | 3/2011 | Moeller-Jensen | A61M 3/0279 604/275 |
| 2001/0021817 | A1 * | 9/2001 | Brugger | A61M 1/3626 604/6.11 |
| 2003/0073963 | A1 * | 4/2003 | Falconer | A61M 3/0262 604/328 |
| 2003/0236489 | A1 * | 12/2003 | Jacobson | G05D 7/0676 604/67 |
| 2004/0191116 | A1 * | 9/2004 | Jarvik | A61M 1/3666 422/44 |
| 2006/0150310 | A1 * | 7/2006 | Tsai | A61M 3/0225 4/420.1 |
| 2006/0224163 | A1 * | 10/2006 | Sutton | A61M 1/74 606/107 |
| 2009/0221986 | A1 * | 9/2009 | Wang | A61M 5/16877 604/503 |
| 2010/0049119 | A1 * | 2/2010 | Norman | A61M 3/022 604/31 |
| 2012/0138832 | A1 * | 6/2012 | Townsend | F16K 7/065 251/251 |
| 2013/0267892 | A1 | 10/2013 | Woolford | |
| 2014/0005602 | A1 * | 1/2014 | Andreen | A61M 3/02 604/98.02 |
| 2014/0188076 | A1 * | 7/2014 | Kamen | A61M 5/16831 604/506 |
| 2015/0335529 | A1 * | 11/2015 | Andersson | A61J 1/1475 206/438 |
| 2016/0114148 | A1 * | 4/2016 | Holm | A61M 39/284 604/250 |
| 2016/0175510 | A1 * | 6/2016 | Patel | A61M 1/3496 137/12 |
| 2016/0220751 | A1 * | 8/2016 | Mallough | A61F 9/00745 |
| 2017/0049959 | A1 * | 2/2017 | Eitan | A61M 5/16854 |

FOREIGN PATENT DOCUMENTS

| | | | |
|---|---|---|---|
| CN | 102631723 A | 8/2012 | |
| CN | 104519925 | 4/2015 | |
| EP | 1531885 | 10/2008 | |
| EP | 2679261 | 11/2016 | |
| JP | 11007323 | 1/1999 | |
| JP | 11019210 | 1/1999 | |
| WO | 20090152568 | 12/2009 | |
| WO | 20140154635 | 10/2014 | |
| WO | 20150175484 | 11/2015 | |
| WO | 20160095929 | 6/2016 | |
| WO | WO-2016095929 A1 * | 6/2016 | ......... A61M 3/0258 |
| WO | WO-2018096373 A2 * | 5/2018 | ............. F16K 7/065 |

OTHER PUBLICATIONS

Office Action for Chinese Patent Application No. 201780055086.X, dated Apr. 24, 2020 (7 pages).
Office Action for Chinese Patent Application No. 201780055086.X, dated Oct. 22, 2019 (14 pages).
Office Action for Japanese Patent Application No. 2019-513788, dated Apr. 27, 2021 (11 pages).

* cited by examiner

MOTORIZED IRRIGATION SYSTEM WITH IMPROVED FLOW CONTROL

CROSS-REFERENCE TO RELATED APPLICATIONS

This patent document claims the benefits and priority to European Patent Convention Application No. 16189171.8, filed on Sep. 16, 2016, which is incorporated herein by reference in its entirety.

FIELD OF INVENTION

The present invention relates to an irrigation system, particularly intended for rectal irrigation, and is suitable for self-administration of an irrigation liquid.

BACKGROUND

Administrating an irrigation liquid is a common medical procedure whereby liquid is injected into a bodily cavity, such as into the rectum and lower intestine of a patient in order to induce bowel movement. The need for such a procedure typically arises in patients suffering from various physical ailments in which voluntary bowel control is impaired or when the bowel needs to be cleaned before, e.g., a coloscopy or a surgical operation. To this end, irrigation systems may be used, e.g., by people suffering from spinal cord injuries, spina bifida or multiple sclerosis. For such users, irrigation may improve quality of life by preventing constipation, reducing time spent for bowel emptying procedures, reducing fecal incontinence, and by increasing independency in general.

Irrigation is nowadays often performed outside medical attendance premises, such as in the patient's home, and is also often performed by the patient himself, i.e. by self-administration. Thus, such irrigation systems need to be easy to control. Further, many of the users of irrigation systems have reduced dexterity, which makes simple operation even more important.

It is further of importance that the irrigation system is of a limited size, and portable. Portability of the irrigation system is important to disabled persons who are not hospitalised or bed-ridden if they are to live as normal a life as possible. This is particularly important if they travel away from their home, for instance, to someone else's home or if they stay in a hotel. In this situation, they need to be able to deal with their bowel function easily.

To this end, it has been proposed to use electrically operated irrigation systems, which simplifies the irrigation process. Electrically operated irrigation systems are, e.g., disclosed in WO 2016/095929, US 2016/0114148, WO 2009/152568 and EP 2 679 261.

However, these systems are also subject to various problems, such as being somewhat complex and expensive. Further, the electrical systems of these known systems are often difficult to control with sufficient precision. For example, the desired flow rate varies widely between users. Sometimes a very limited flow rate is desired, whereas in other situations and for other users, a relatively high flow rate is desired. Thus, there is a need to control the flow rate with high precision and accuracy, and to provide a constant flow rate, with no or small variations during the irrigation process, at the set level. However, in known systems, this is difficult to achieve.

Some known irrigation systems use indirect pumping, i.e. where a fluid such as air is pumped into a reservoir holding the irrigation liquid, and thereby increasing the pressure in the reservoir so that the irrigation liquid is pumped out from the reservoir. Such indirect pumping has many advantages compared to direct pumping, such as being easier to operate, less costly etc. However, it has been found that such irrigation systems using indirect pumping are particularly difficult to operate with adequate precision, e.g., in order to obtain a constant and exact flow rate.

It may also be difficult to ensure that the irrigation system is always operated in a safe way, and unintended use of the system, either on purpose or by accident, may lead to discomfort or even hazard to the user/patient.

There is therefore a need for an irrigation device which can be used safely, easily and conveniently, and with improved controllability, for self-administration of the irrigation liquid, and which also preferably can be produced in a cost-efficient way.

SUMMARY

In view of the above mentioned need, a general object of the present invention is to provide an irrigation system which alleviates the above-discussed problems of the prior art, and at least partly fulfils the above-discussed needs.

This and other objects are achieved with an irrigation system according to the appended claims.

According to a first aspect of the disclosed technology, there is provided an irrigation system comprising:
  a reservoir for an irrigating liquid;
  a probe for arrangement in a user;
  tubing providing fluid communication between said reservoir and said probe;
  an electrical pump for indirectly pumping irrigation liquid from the reservoir to the probe through said tubing, said electrical pump being controllable to assume a plurality of predetermined flow rates;
  an electrically operable valve operable to continuously control the degree of openness of said tubing between a fully closed state and a fully opened state;
  a flow sensor to measure an actual flow rate of the irrigation liquid in the probe; and
  a controller arranged to obtain a desired flow rate from a user interface, and configured to control the flow rate of the electric pump to one of said plurality of flow rates exceeding said desired flow rate, and to continuously regulate the electrically operable valve based on the measured actual flow rate, thereby limiting the flow rate provided by the electric pump to obtain said desired output flow rate.

In some implementations, a double control of the flow rate is provided. A first, coarse control of the flow rate is provided by controlling the electric pump. This may, e.g., be obtained by controlling the voltage provided to the pump. The pump may, e.g., be controllable to assume two, three, four, five or more predetermined flow rates. The pump may also be controllable to assume multitude of predetermined levels, or even be continuously controllable to assume any flow rate within a certain range or the like. A second, finer control of the output flow rate is then provided by controlling degree of openness of the electrically operable valve. The valve is preferably controlled by a feedback control system, wherein the output flow rate is determined by the flow sensor, and the electrically operable valve is controlled by the controller in real-time to adjust the degree of openness in accordance with the input from the flow sensor.

In this way, a very precise and accurate control of the output flow rate can be obtained within a broad range of possible desired flow rates. For example, the flow rate can be controlled to be as low as 100 ml/min, or even lower, and as high as 700 ml/min or even higher.

The electric pump is arranged for indirect pumping of the irrigation liquid. Hereby, the pump pumps a different fluid, such as air, into the reservoir, thereby increasing the pressure in the reservoir, and as a consequence forcing irrigation liquid out from the reservoir, for discharge through the probe. For example, the electric pump may be arranged to pump a gas, and preferably air, into the reservoir to create a pressure in the reservoir to displace the irrigation liquid therefrom and feed it to the probe.

An electric pump is of great advantage in irrigation systems of this type, since it can be operated very easily, which is particularly advantageous for users with reduced dexterity. If the user lacks strength in their hands it may be easier for them to operate an electric pump rather than squeezing, e.g., a foil-pump. The electric pump can also easily be adjusted and customized for different types of use, for different types of users, etc.

It has been found by the present inventors that controlling the flow rate by only controlling the electric pump is often insufficient, and in particular when indirect pumping is used. It is often difficult to provide a flow rate with adequate precision, the flow rate is often unstable over time, and it is very difficult to obtain low flow rates, such as below 250 ml/min. The flow rate also often varies from time to time, or even during an irrigation process, due to changes in the contextual environment. For example, a higher flow rate is normally obtained if the reservoir is at a higher position in relation to the probe, such as being placed in a sink, on a table or the like, whereas a lower flow rate is normally obtained if the reservoir is at a lower position in relation to the probe, such as being placed on the floor. The counter pressure in the colon may also vary between different users, as well as over time for one and the same user.

However, by using the additional flow rate control provided by the electrically operable valve, any desired flow rate can be obtained within a very large range, and with a very high precision and stability. Further, the control will automatically adjust to contextual variations, such as variations in the counter pressure of the colon.

Further, by controlling the flow rate also by the electric pump, several advantages are obtained. The power consumption is reduced, thereby providing better use of the capacity of batteries or other power sources. Thus, the battery will last longer after having been charged, and do not need to be recharged as frequently. Additionally or alternatively, less costly batteries with less capacity may be used and still provide the same operation time.

Further, the double control provides increased safety for the user. Should one of the controls fail, such as the voltage to the electric pump be inadvertently turned to its maximum, the valve become fully opened or the like, the effect on the output flow rate will be limited, and the risk of inconvenience or even hazard to the user will be very limited even in extreme types of failures.

Still further, the new irrigation system facilitates operation, in particular for users having reduced dexterity. The whole irrigation procedure hereby becomes easier, faster and easier to control.

The controller is preferably arranged to control the flow rate of the electric pump to the one of said plurality of flow rate exceeding said desired flow rate which is closest to the desired flow rate.

The electrical pump is preferably controllable to assume at least four predetermined flow rates.

The controller may be arranged to control the flow rate of the electric pump to the one of said plurality of flow rate exceeding said desired flow rate by less than 25%, and preferably with less than 15%, and most preferably with less than 10%.

The electrical pump is preferably controllable to assume a plurality of predetermined flow rates by control of the voltage supplied to the electric pump.

Many types of electrically operable valves can be used in the above-discussed irrigation system. However, preferably the electrically operable valve is a clamping or pinch valve, providing a controllable clamping/pinching action on a tube leading between the electrical pump and the probe. For example, the valve may be of the type disclosed in US 2006/0114148 by the same applicant, said document hereby being incorporated in its entirety by reference.

Thus, the valve preferably comprises a clamping/pinching structure for a conduit or a tube. The terms "conduit" and "tube" are in the following used to indicate a structure enclosing a lumen, and being made of at least somewhat flexible material. The cross-sectional shape is preferably circular, but other shapes, such as oval, may also be provided.

In one embodiment, the electrically operable valve comprises a movable arm that is connected to a constriction structure, said constriction structure being arranged opposite to an abutment, and with the tube extending between said constriction structure and said abutment, whereby movement of the moveable arm moves the constriction structure to control compression of the tube between said constriction structure and said abutment. The moveable arm may be movable in any suitable direction, such as being moveable longitudinally, e.g., by means of a linear motor, or be rotatable, e.g., by means of a servo motor. In a preferred embodiment, the moveable arm is rotatable, and comprising a cam shape engaging said constriction structure.

The probe may be provided with an inflatable retention member. Inflation of the inflatable retention member may be effected by the same electrical motor being used for pumping the irrigation liquid. Alternatively, a second pump may be provided for inflation of the inflatable retention member. In this case, the second pump may also be an electric pump, or alternatively be a manually operated pump, such as a bulb or a bellow pump.

The irrigation system may further comprise a control unit with a housing, the housing enclosing at least the electrical pump, the electrically operable valve, the flow sensor and the controller.

The tubing preferably includes a first part connecting the control unit with the probe and a second part connecting the reservoir with the control unit, and in which each of the first and second parts comprises a gas conducting tube and an irrigating liquid conducting tube. Hereby, gas can be pumped from the electric pump in the control unit to the reservoir, irrigation liquid may be transferred from the reservoir to the irrigation probe, via the electrically operable valve, and a gas may be pumped from the control unit to the inflatable retention member of the probe.

The tubing is preferably arranged so that the control unit is arranged at a distance from both the reservoir and the probe, and being connected to the reservoir and probe, respectively, through the tubing. This makes it possible to have the reservoir at a distance from the control unit, e.g., on the floor, and still provide a good working position for the user.

The control unit further preferably comprises control elements for operation of the irrigation system. Preferably, the control unit comprises control elements for pumping of irrigation liquid, and optionally for inflation and deflation of the inflatable retention member. The control unit may also comprise control elements operable to set the desired flow rate. However, alternatively, the desired flow rate may be set through a remote control or the like.

The control unit further preferably comprises a display. The display may be used to display information to the user about the progress of the irrigation procedure, such as volume that has been pumped, present flow rate, time elapsed from the start of the procedure, or estimated time left, etc. Further, the display may be used to guide the user about what choices in terms of settings and the like that are needed, the present function of the control elements, etc. Still further, the display may be a touch screen, useable also for inputting data into the system. For example, the control elements may be realized as areas on the touch screen. If the control unit is connected wirelessly to a remote control or other remote unit, the display on this device may be used to display information as well. Thus a display on a remote control or other remote unit may be used to replace the display on the control unit, or to complement a display on the control unit.

In a preferred embodiment, the control unit comprises a valve for releasing fluid from the retention member for deflation, said valve being controllable by a control element, and preferably a control button.

At least one, and preferably both, of the control element for controlling pumping of the irrigation liquid and the optional control element for pumping fluid for inflation of the inflatable member preferably functions as a dead man's handle, thereby immediately returning to a deactivated state, in which the electrical pump is controlled not to pump, when manual operation of the control element is aborted. The control element(s) for inflation and deflation of the inflatable retention member may further be arranged as separate control elements. By means of this dead man's handle functionality it is ensured that pumping is immediately aborted when the control element is released. This means that the pumping action is stopped immediately when the control element is released, regardless of whether this release is intentional or by accident. For example, the pumping will stop immediately if the control element is accidentally dropped. Further, stopping by releasing is a very intuitive and quick operation method, which is both ergonomically favourable and fast.

The control elements are operable by applying a predetermined condition to bring the control element into the activated state, and preferably at least one of depression, twisting, rotating, pulling and pushing. If a control button is used, the predetermined condition is preferably depression, so that the control button is activated by depressing it, and deactivated by releasing it. However, alternative types of control elements, such as rotatable knobs, switching levers and the like may also be used. An automatic return to the deactivated state when the predetermined condition ceases can, e.g., be obtained by a spring, an elastic element, or the like, operable to provide a counterforce to the force applied by the manual operation. The control elements, such as control buttons, may be arranged on the surface of the housing. The control elements may, e.g., be realized as areas on a touch screen.

The control unit preferably comprises at least two control elements, such as control buttons, and preferably at least three control elements. Two, or preferably three, control elements enables a very easy manipulation of the control unit, and at the same time provides numerous input alternatives. It is further preferred that at least one of the control element(s) is a multi-purpose control element having different functions in different operation states. Hereby, the control elements can, e.g., be assigned to control different functions during initiation/set-up and during operative use.

One or several control elements may also be arranged separated from the control unit, and may, e.g., be connected with the control unit by means of wire, and thereby be physically connected to the electric pump etc. Alternatively, the control elements may be arranged on a remote control, which is wirelessly connected to the rest of the irrigation system. The remote control can, e.g., be at least one of: a smart phone, a tablet computer and a laptop computer. It is also possible to combine a control unit with integrated control elements and a remote control, whereby the user may chose whether to use the integrated control unit or the remote control, or both, for controlling the irrigation process.

By the use of a remote control, the control unit may, e.g., be placed on the floor, or in any other resting position, and instead be operated through the remote control during irrigation. This facilitates handling of the irrigation system, and affords the user an increased freedom in terms of how to use the system. The remote control may be a dedicated remote control, specifically arranged to control the irrigation system. However, the remote control may also be a common wireless device, capable of transmitting wireless control signals to a receiver in the control unit. In one preferred embodiment, the remote control is a mobile telephone, and preferably a smart phone. Additionally or alternatively, the remote control may be a laptop computer or a tablet computer. Hereby, a special application may be downloaded to the smart phone/laptop/tablet computer, providing a suitable interface for the device, and enabling it to send appropriate control signals to the control unit.

The wireless communication between the control unit and a remote control or a remote unit may be obtained in many ways, as is per se well known in the art, such as by infrared light (IR), ultrasonic communication, radio frequency (RF) communication, such as Bluetooth, etc.

The control unit may further be arranged to transmit operation related data to a remote unit via wireless communication. For example, such data may be sent to a smart phone or the like. Hereby, the irrigation procedures may, e.g., be logged over time, to facilitate follow-ups and also enabling a more adequate setting of parameters for forthcoming irrigations.

The control unit is further preferably provided with a battery for driving the electric pump.

The control unit may further comprise a waterproof housing enclosing at least said battery and wherein, the electrical system of the irrigation system is galvanically isolated from the exterior of the irrigation system, and wherein the battery is chargeable through inductive charging. Such a waterproof housing and galvanic separation between the electric system and the surrounding environment makes the system very robust. It can hereby withstand for example spilling of water, or even accidental submersion of the control unit etc. in water. Since an irrigation system is typically used in close relation to water and other liquids, this is an important advantage. This also makes it possible to use the system, or components of the system, for longer time, which provides a better overall cost-efficiency.

Inductive charging uses an electromagnetic field to transfer energy from a charging station to the battery to be charged. Energy is sent through an inductive coupling to a receiving circuit within the control unit, which then uses the received energy to charge the battery. For charging, the control unit may be placed on or close to a charging station.

However, it is also feasible to charge the battery by conventional, wired charging. It is also feasible to power the irrigation system during use from an external source, such as being plugged in to the ordinary power supply system. In this case, the battery may even be omitted.

The controller is preferably programmable. For example, the controller may be programmable to set the desired flow rate. Further, the controller may be programmable to set total irrigation liquid volume to be discharged. The controller may be pre-programmed with a number of programmes or it may be programmed via the control element(s) or through an external remote control or the like. The controller may be programmable so as to automatically carry out a predefined program. A user that frequently uses anal irrigation may experience a preferred way of carrying out the irrigation process. Then it is of advantage to be able to programme this way into the controller, so that the irrigation process is done the most preferred way every time. Furthermore, caregivers may have a certain experience concerning the optimum process, which they can programme into the controller. Thereby errors will be reduced.

Further, the controller may be programmable to set a maximum filling level of the inflatable retention member. The maximum filling level may be a fixed level, defined by the producer, a physician or the like, or a user defined, customizable level, determined by the user, or a combination of both. This increase the safety of the irrigation system, since inadvertent overfilling of the inflatable retention member can hereby be avoided.

Preferably, all components of the irrigation system are individually exchangeable, so that, e.g., the probe/catheter can be exchanged frequently, and typically be used only once, whereas other parts of the system, such as the control unit, the electrical system and the irrigation liquid reservoir can be used for months or even years.

The irrigation system comprises relatively few and uncomplicated components, and which may be reused for a long time, which makes the irrigation system relatively easy and cost-efficient to produce. Further, the irrigation system lends itself well for automated or semi-automated manufacturing.

The irrigation system is also highly suitable for self-administration of the irrigation liquid. The control elements on the control unit also make it easy to access the pump with one hand only, and to switch between different pumping modes etc. Typically with this arrangement, it is, e.g., possible to operate the irrigation system with one finger, e.g., the thumb. This provides a very convenient and precise controllability of the irrigation system.

According to another aspect of the disclosed technology, there is provided a method for controlling an irrigation system comprising:
- obtaining a desired flow rate to be irrigated out from a probe;
- controlling the flow rate of an electric pump to provide a flow rate exceeding said desired flow rate;
- measure the actual flow rate of the irrigation liquid in the probe; and
- controlling, continuously, an electrically operable valve based on the measured actual flow rate, thereby limiting the flow rate provided by the electric pump to the desired flow rate.

With this aspect, similar advantages as discussed above in relation to the first aspect are obtained.

The electric pump is preferably controllable to assume a plurality of predetermined flow rates, and wherein the flow rate of the electric pump is controlled to one of said plurality of flow rate exceeding said desired flow rate.

According to aspects of the disclosed technology, there is provided a use of the irrigation device as discussed above for rectal irrigation.

These and other aspects will be apparent from and elucidated with reference to the embodiments described hereinafter.

BRIEF DESCRIPTION OF THE DRAWINGS

For exemplifying purposes, the disclosed technology will be described in closer detail in the following with reference to embodiments thereof illustrated in the attached drawings, wherein.

DETAILED DESCRIPTION OF PREFERRED EMBODIMENTS

Figure 1:
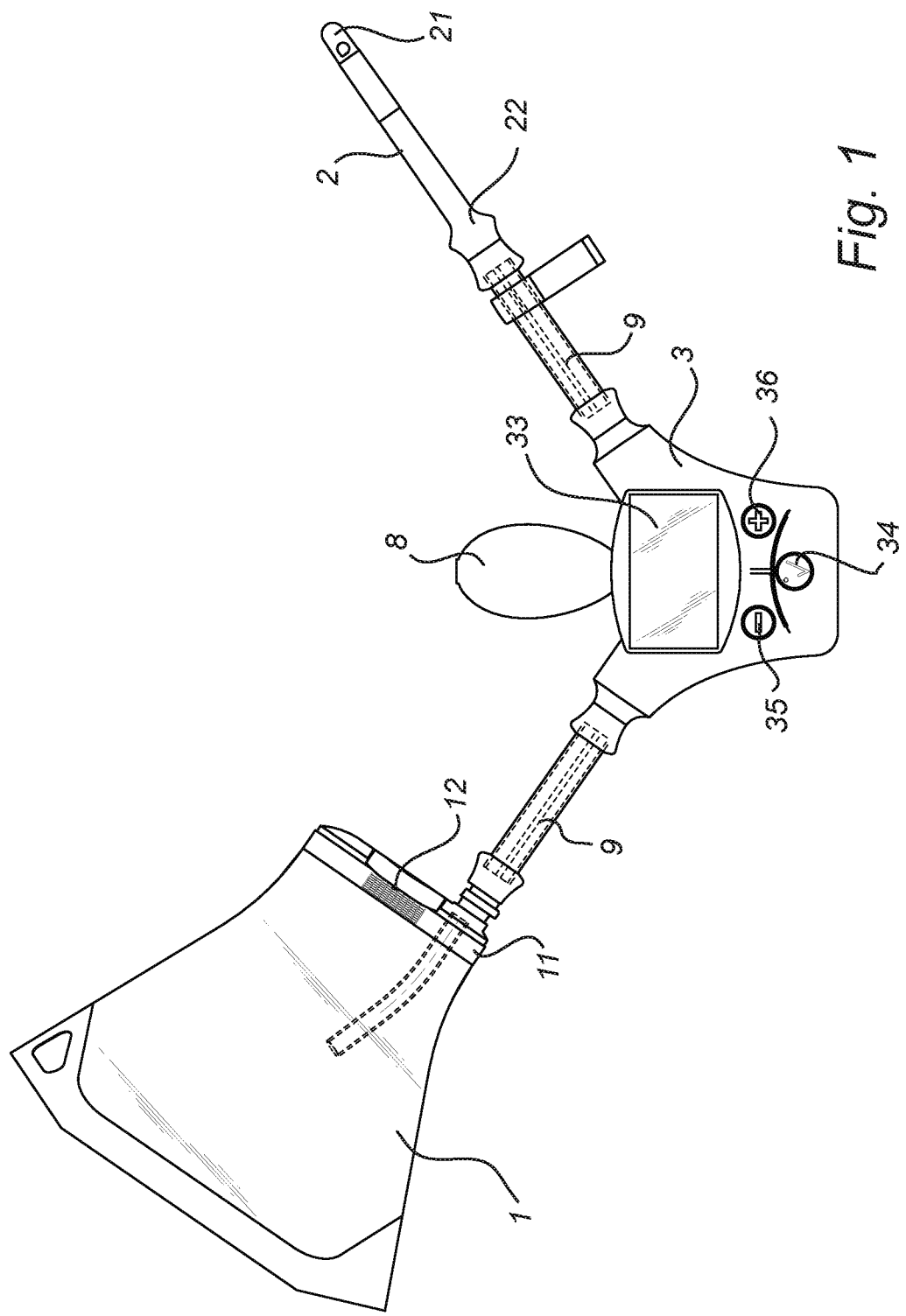
FIG. 1 is schematic overview of an irrigation system according to a first embodiment in accordance with the disclosed technology.

The disclosed technology is directed to motorized irrigation systems and methods with improved flow control that will now be described more fully hereinafter with reference to the accompanying drawings, in which currently preferred embodiments of the disclosed technology are shown. This disclosed technology may, however, be embodied in many different forms and should not be construed as limited to the embodiments set forth herein; rather, these embodiments are provided for thoroughness and completeness, and fully convey the scope of the present technology to the skilled addressee. Like reference characters refer to like elements throughout. Further, in the following, an irrigation system, particularly useful for rectal irrigation, will be discussed. However, it is to be acknowledged by the skilled reader that the same control system and control method may also be used for other types of irrigation systems and the like.

FIG. 1 discloses an irrigation system according to a first exemplary embodiment, comprising a reservoir 1 for an irrigating liquid, a probe 2 for arrangement in a user, and a control unit 3. Tubing 9 is arranged to connect the reservoir 1 with the control unit 3 and the control unit 3 with the probe 2.

The reservoir may be realized in various ways. For example, the reservoir may be formed by a rigid, semi-rigid or flexible material. In case a semi-rigid or flexible material is used, the reservoir may be collapsible or foldable, to make the irrigation system more compact prior to use. The reservoir is provided with an opening, closed by a lid 11, for filling of the reservoir. Tubing connecting the reservoir to the rest of the irrigation system may be provided through the lid 11, or through other access points on the reservoir.

As one embodiment, the reservoir may be a collapsible reservoir of the type disclosed in US 2015/335529, said document hereby being incorporated in its entirety by reference.

In order to render the irrigation system as portable as possible, the container preferably has a capacity of less than 5 litres, more preferred less than 3 litres and most preferred less than 2 litres. If however the system is to be used for repeated irrigation, a larger capacity container may be necessary.

The reservoir may comprise an overpressure release valve, to release pressure over a predetermined maximum pressure to be allowed. Further, the reservoir preferably comprises a filter 12, such as a hydrophobic filter, which is impermeable to the irrigation liquid, but which allows air to enter the reservoir but not escape the reservoir. Such a filter ensures that the reservoir maintains its shape when irrigation liquid is being pumped out from the reservoir. This is of advantage, since it makes the reservoir more stable. It also makes it possible to use less costly materials and less rigid containers when producing the reservoir, thereby making the production more cost-efficient. This ensures that the reservoir remains stable during irrigation. However, alternative means for obtaining this are also feasible. For example, the reservoir may simply be provided with an air inlet, possibly provided with a back-valve to prevent outflow of irrigation liquid, should the irrigation liquid reach the inlet.

The probe 2 is here embodied as a rectal catheter. The probe is preferably provided with a retention member, such as an inflatable balloon 21, for fixing the catheter in a body cavity. Further, the probe may be provided with a rearward enlarged part 22, providing an abutment to hinder too deep insertion. The probe is preferably provided with two lumens—one lumen for transfer of irrigation liquid through the probe, for discharge at the forward end, and one lumen for inflation and deflation of the balloon.

The probe may be of the type disclosed in WO 2014/154635, said document hereby being incorporated in its entirety by reference.

An electric pump 4 (shown in FIG. 3) for pumping irrigation liquid is here provided within the control unit, but may also be arranged outside the bounds and housing of the control unit. The pump is part of the electrical system of the irrigation system, connecting the pump inter alia to a battery. The electrical system is disclosed in further detail with reference to FIG. 3 in the following. The pump is arranged to pump gas, e.g., air, into the reservoir to create an overpressure, which forces irrigation liquid in the reservoir to be transferred to the probe. Such a system is, e.g., disclosed in EP 1 531 885, said document hereby being incorporated in its entirety by reference.

The control unit is here realized as a unitary, hand-held unit. The control unit comprises a display 33, and three control elements 34, 35 and 36. The control element is preferably realized as a depressible control button. The control unit is preferably waterproof. The control elements may thus be realized with thick pliable plastic or the like, designed to withstand many pushes. The further details and function of the control unit will be discussed in more detail in the following.

In this embodiment, a second pump 8 is arranged to pump fluid into the balloon of the probe. The pump is a manually operable pump. However, other types of pumps are also feasible for use as the second pump, such as electric pumps, pneumatic pumps and the like. In the shown example, the manually operable pump is a bulb pump, comprising an inlet, provided with a one-way valve, allowing a fluid to enter but not exit the pump. Further, the pump comprises a pumping compartment and outlets, provided with a one-way valve, allowing a fluid to exit but not enter the pump. The pumping compartment is made of a resilient, squeezable material, which retains it shape when unloaded. By squeezing the pumping compartment, the fluid is pumped out through the outlet, and when the squeezing is relieved, the pumping compartment retains its original shape, thereby sucking in fluid through the inlet. In the illustrative example, the pump is used to pump air. Thus, the second pump 8 pumps air into the balloon 21 for inflation. The air is releasable through a valve, which is controllable by one of the control elements, e.g., control element 34.

The control elements 35 and 36 may here be used to activate the pump for transferring of irrigation liquid through the probe for irrigation (control element 36), and for releasing overpressure and/or draining the system from remaining liquid (control element 35). Thus, inflation and deflation of the retention member may take place independently of the irrigation, and, e.g., simultaneously.

Tubing is arranged to connect the reservoir, control unit and probe together. Preferred materials for the bulb pumps and the balloon can be any suitable material, e.g., such as PVC, latex, TPE or PU. However, other materials providing similar properties can likewise be used.

Figure 2:
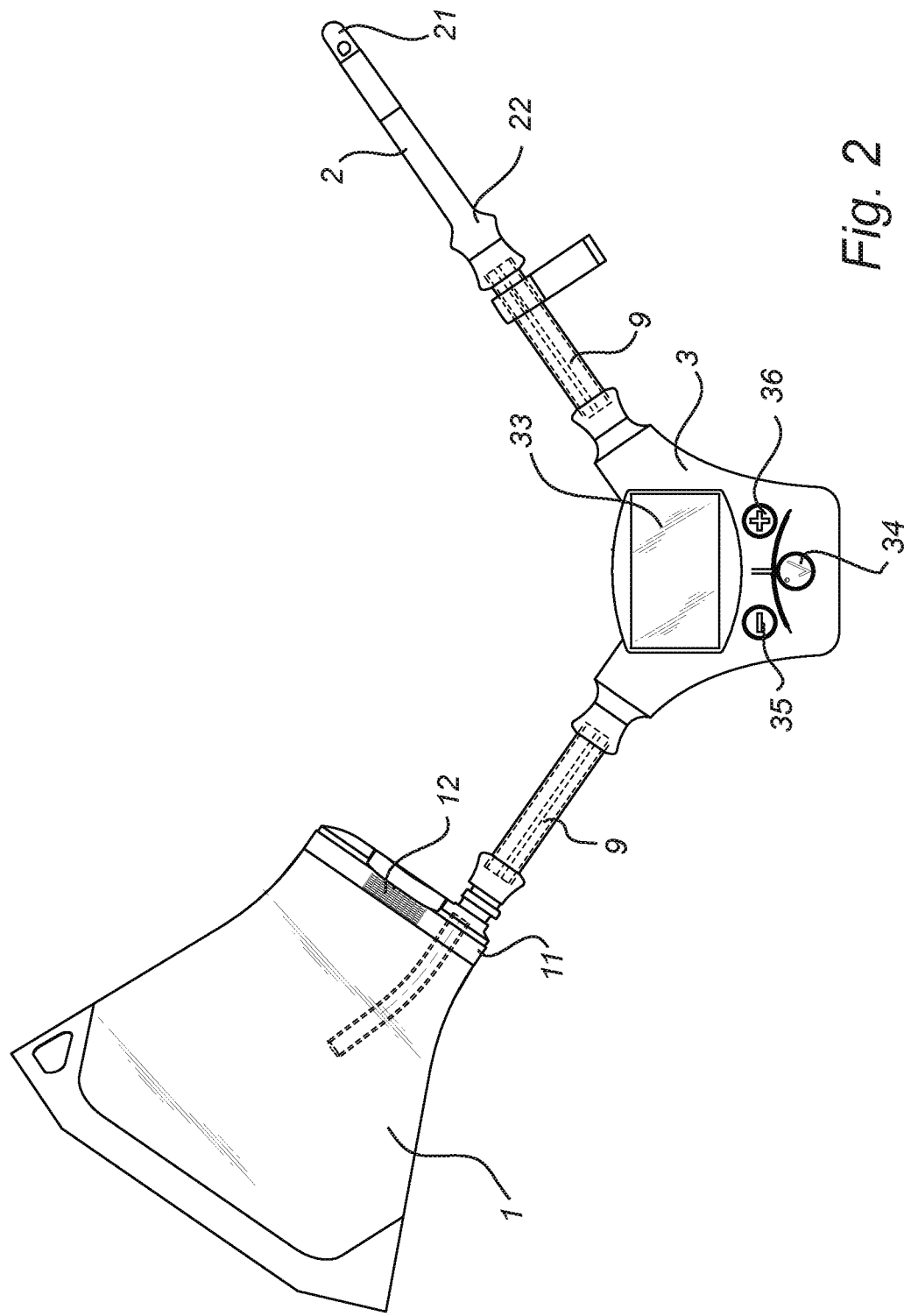
FIG. 2 is a schematic overview of an irrigation system according to a second embodiment in accordance with the disclosed technology.

The second embodiment, illustrated in FIG. 2, resembles the above-described first embodiment. However, here the electrical pump 4 is also useable to inflate the balloon 21 of the probe. Consequently, there is no need for the second pump 8.

The irrigation liquid can be any liquid which is capable of irrigation the body cavity of interest. In order to stimulate bowel movements suitable irrigation liquids includes water, hypertonic aqueous salt solutions, solutions or suspensions of cathartic agents, such as bisacodyl or phenolphthalein, and mineral oil.

Figure 3:
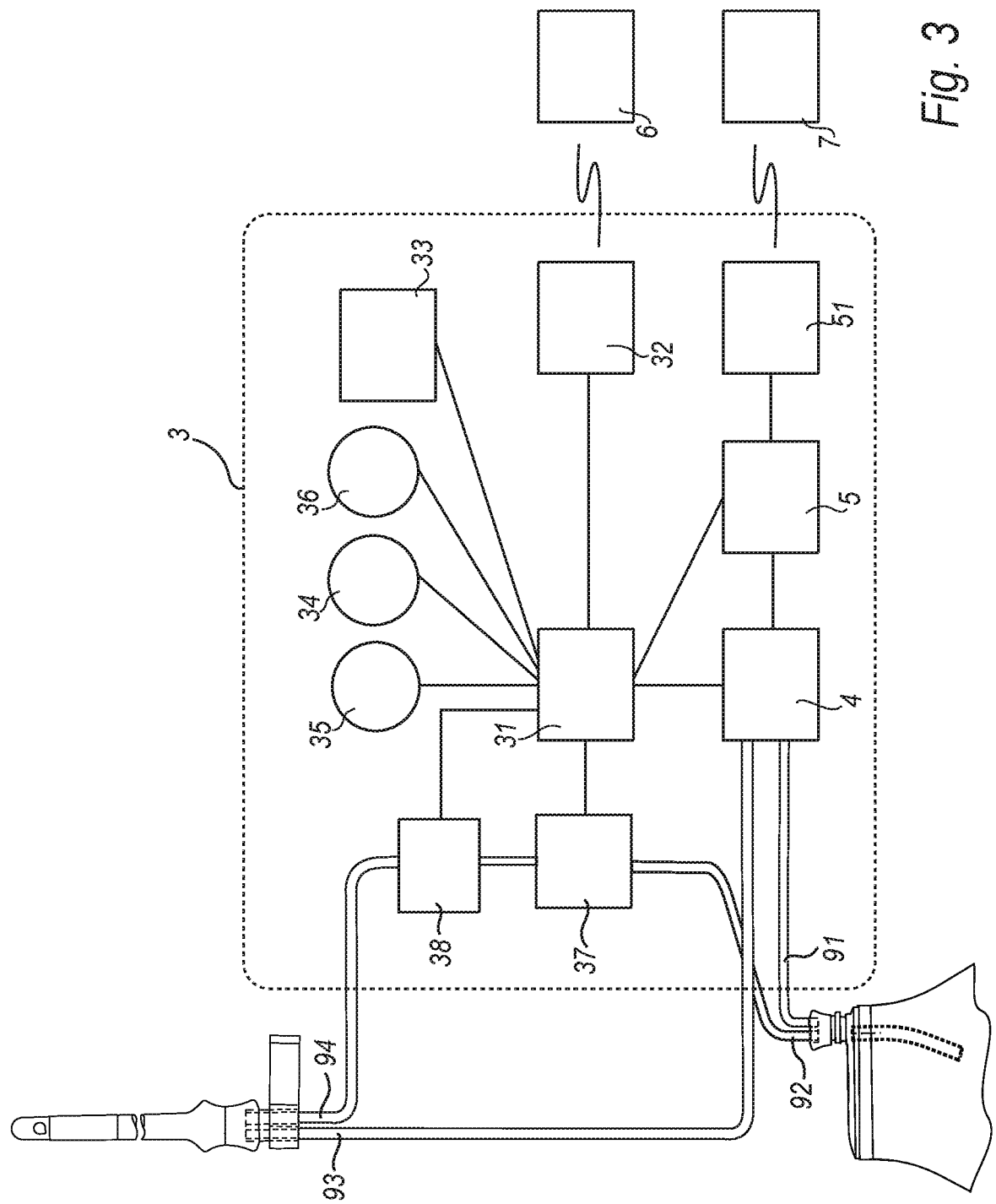
FIG. 3 is a schematic overview of a control unit for use in an irrigation system according to some embodiments in accordance with the disclosed technology.

The electrical system of the irrigation system will now be discussed in more detail, with reference to FIG. 3. The electrical system is arranged within the housing of the control unit 3, and comprises an electric pump 4, as previously disclosed, connected to a battery 5 and a controller 31, such as a micro-processor. The controller 31 is further connected to the display 33, and to switches activated by means of the control elements 34-36. Further, the controller is optionally connected to a wireless transceiver 32, which is adapted to transmit and receive data from a remote unit 6. Hereby, the remote unit may provide control data to the controller 31, for remote control of the control unit. Additionally or alternatively, the controller may transmit data about the irrigation procedure to the remote unit. The remote unit 6 may, e.g., be a remote control, a smart phone or the like. The battery 5 is further connected to a charging circuit 51, adapted to receive inductive charging from a charging station 7. All elements of the electrical system are connected by electrical wires. Further, the electrical system is preferably galvanically isolated from the rest of the irrigation system and the environment.

At least the control element used to operate the electric pump is preferably provided with a dead man's handle functionality. Thus, the control element is brought into the activated state by continuous application of a predetermined condition thereto, and is immediately brought to the deactivated state when the predetermined condition ceases to be applied, thereby aborting pumping of the irrigation liquid. In addition, some or all of the other control elements may also be provided with dead man's handle functionality. The automatic return to the deactivated state when the predetermined condition ceases can, e.g., be obtained by a spring, an elastic element, or the like, operable to provide a counterforce to the force applied by the manual operation.

The electric pump 4 is arranged to pump a fluid, and preferably a gas, such as air, through a conduit 91 to the reservoir. Thereby, pressure increases in the reservoir to pump irrigation liquid through conduit 92 to the control unit. The conduit 92 passes through an electrically operable valve 37 and a flow sensor 38, and continues as conduit 94 to the probe, for dispensing the irrigation liquid to the user.

The tubing 9 further comprises a conduit 93 leading from the control unit to the probe for inflation of the inflatable retention member. In the illustrated embodiment, the conduit 93 is connected to the pump 4, whereby the pump serves both the purpose of pumping air or the like to the reservoir and for pumping air or the like to the inflatable retention member. However, alternatively the conduit 93 can be connected to a separate pump, such as a second electric pump provided in the control unit, the manually operable pump 8, or the like.

The electrically operable valve 37 and the flow sensor 38 are both connected to the controller 31, whereby measurement data is sent from the flow sensor 38 to the controller 31, and the electrically operable valve 37 is controlled by the controller 31 based on this input.

The flow sensor 38 may be any type of flow rate measurement device or flow meter capable of measuring the flow rate of the liquid passing through the sensor. The sensor may, e.g., be a mechanical flow meter, such as a rotary piston meter, a turbine flow meter, or the like, a pressure based meter, such as a linear resistance meter, an optical flow meter, or other types of per se known flow sensors.

The electrically operable valve 37 can be realized in many ways, as is per se well-known in the art. For example, the electrically operable valve may be a clamping or pinch valve, providing a controllable clamping/pinching action on a tube leading between the electrical pump and the probe. For example, the valve may be of the type disclosed in US 2006/0114148 by the same applicant, said document hereby being incorporated in its entirety by reference.

Figure 4:
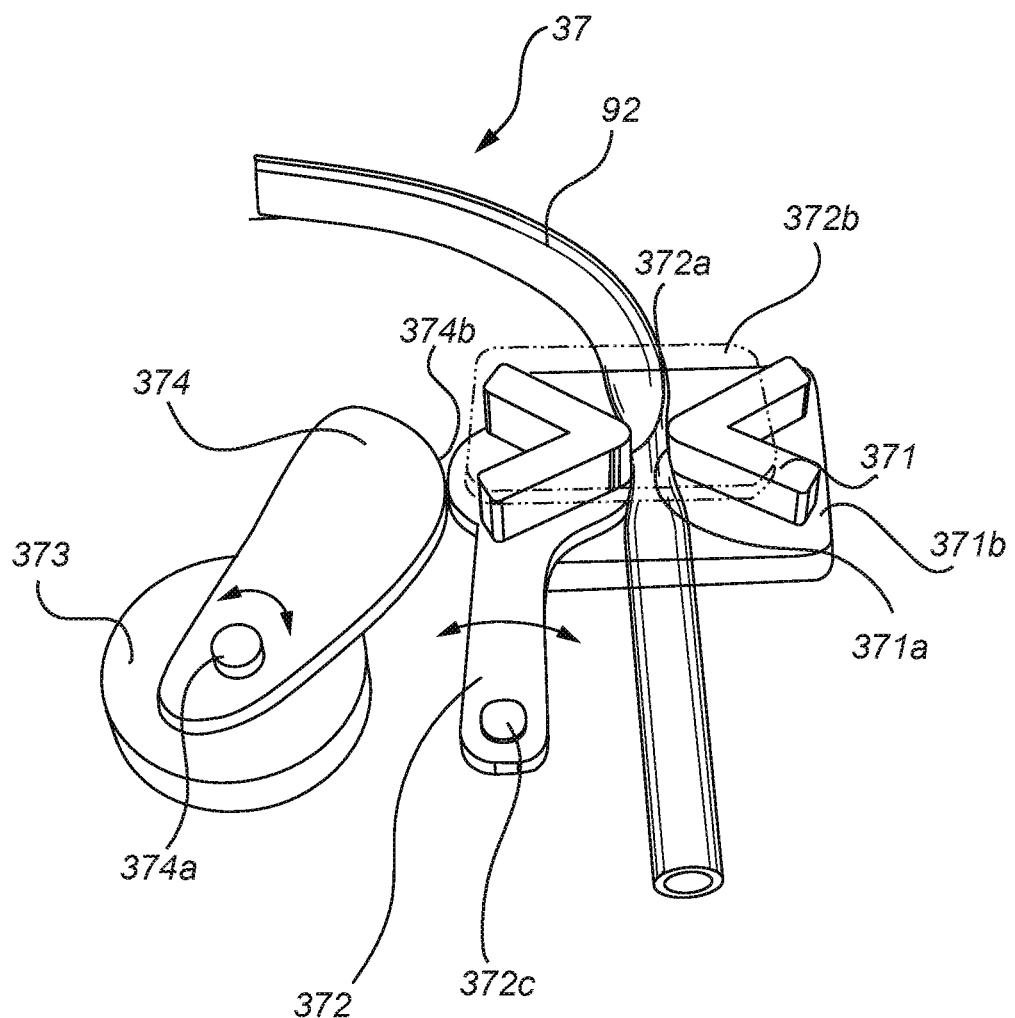
FIG. 4 is a schematic overview of an electrically operable control valve for use in an irrigation system according to embodiments in accordance with the disclosed technology.

In one embodiment, as shown in FIG. 4, the electrically operable valve 37 operates on the conduit 92. The conduit is arranged between a fixed abutment 371 and a moveable constriction structure 372. The abutment 371 preferably forms a relatively sharp abutment surface 371a, such as a tapering and preferably relatively sharp edge, facing the conduit and the constriction structure. Further, the abutment 371 may comprise a protruding support plate 371b underlying or overlying the conduit, thereby supporting and maintaining the conduit between the abutment and the constriction structure. The constriction structure 372 also preferably comprises a relatively sharp clamping surface 372a, such as a tapering and preferably relatively sharp edge, facing the conduit and the abutment. Further, the constriction structure 372 may also have a protruding support plate 372b underlying or overlying the conduit, arranged on the opposite side in relation to the support plate 371b of the abutment, thereby supporting and maintaining the conduit between the abutment and the constriction structure. However, alternatively the conduit may be stabilized by other structure surrounding the valve, in which case one or both of the support plates may be omitted. Still further, it is also possible to provide both support plates on the abutment, or alternatively provide both support plates on the constriction structure.

The constriction structure 372 is moveable in relation to the abutment, so that the distance between the abutment surface 371a and the clamping surface 372a can be controlled between a fully opened position, where the abutment surface and the clamping surface are relatively far from each other, and where the conduit is not constricted, a totally closed position, where the abutment surface and the clamping surface are relatively close to each other, and where the conduit is totally constricted, and any intermediate positions there between, providing semi-closed position having various degrees of constriction.

The movement of the constriction structure may be controlled in various ways. For example, a guide channel or the like may be provided, defining a linear path of movement for the constriction structure toward and away from the abutment. However, in the illustrative example, the constriction structure is instead rotatable around a pivot point 372c, arranged laterally displaced from the clamping surface. Hereby, rotation of the constriction structure towards the abutment brings the clamping surface closer and closer towards the abutment surface, whereas rotation of the constriction structure away from the abutment instead increases the distance between the clamping surface and the abutment surface.

Movement of the constriction structure is controlled by the controller 31, and can, e.g., be effected by means of an electric motor 373. In the illustrative example, the electric motor is an electric servo motor, operable to rotate a moveable arm 374 towards and away from the constriction structure. The moveable arm 374 is here rotatable around a pivot point 374a, which is driven by the electric motor 373. The moveable arm 374 comprises a cam shape 374b, engaging the constriction structure 372. Thus, the moveable arm moves the constriction structure to control compression of the tube between the constriction structure and the abutment. However, the moveable arm may alternatively be movable in other ways. For example, the moveable arm may be moved longitudinally, in which case the electric motor may be realized as a linear motor.

The elasticity of the conduit will in most cases, dependent on the material of the conduit, be sufficient to bring the clamping surface back when the pressure of the moveable arm decreases, thereby automatically and gradually bringing the valve back to an opened position. However, in case the elasticity is insufficient to this end, a spring or the like may be provided, exerting a counteractive force in relation to the force exerted by the moveable arm.

The number of control elements, and the configuration of the control unit, may naturally be made differently. It is also possible to use other types of control units, and to implement, e.g., the flow rate control in relation to other types and configurations of control elements. One such alternative embodiment of a control unit is illustrated in FIG. 5.

Figure 5:
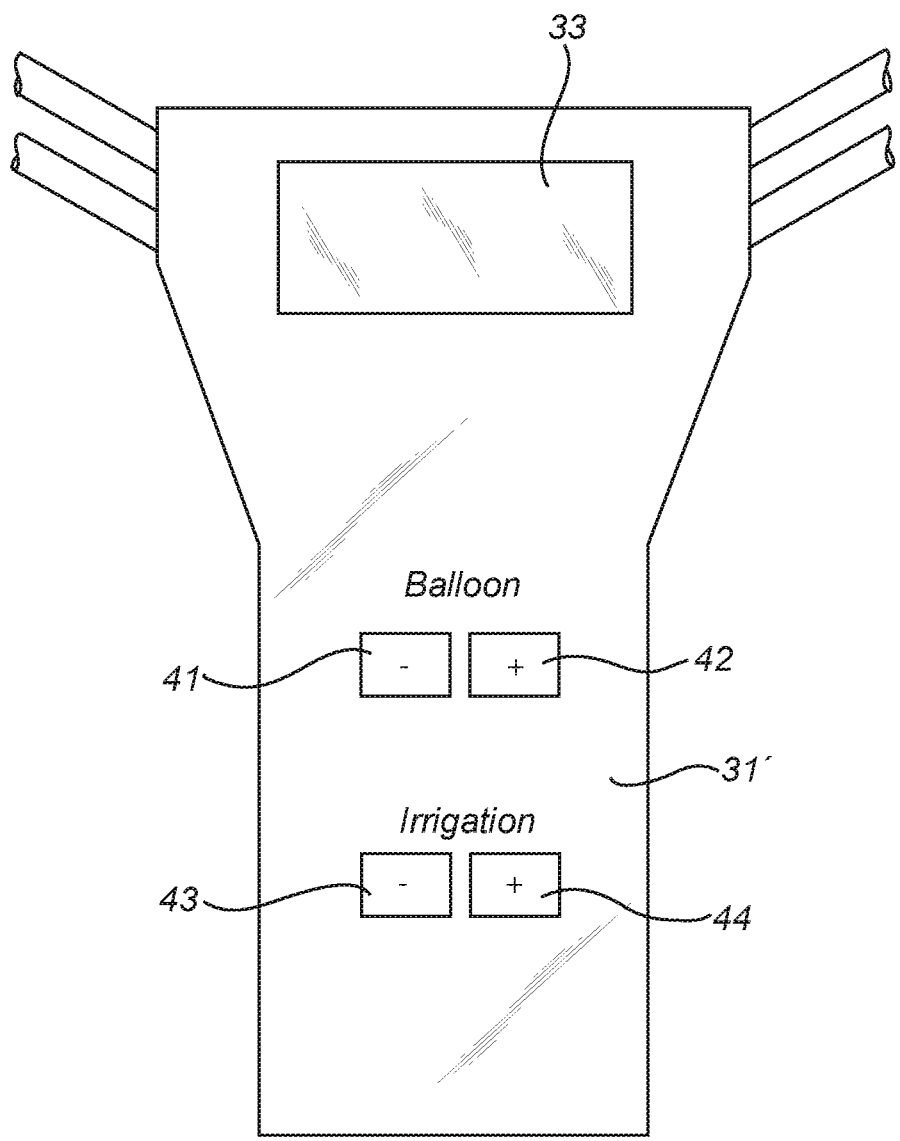
FIG. 5 is a schematic overview of an alternative embodiment of a control unit useable in irrigation systems in accordance with the disclosed technology.

In the control unit of FIG. 5, the control unit 31' is provided with separate control elements, here in the form of control buttons, for irrigation and for inflation/deflation of the balloon on the probe, respectively.

It is possible to use the same control element for both inflation and deflation of the probe, e.g., by using a rocker lever or the like, having three states—inflation, deflation and non-operative. The non-operative state should be default, and as discussed above, the non-operative state should preferably automatically be resumed as soon as the control element is released. However, preferably separate control elements, such as buttons are used for inflation and deflation, respectively. In the illustrative example, a first button 41 is used for deflation of the balloon, and a second button 42 is used for inflation of the balloon. Again, the buttons are preferably only operative when depressed, and release of the buttons will preferably immediately stop the inflation/deflation processes.

Similarly, the irrigation is controlled by one or several control elements. For irrigation, only one operation is normally required, viz. to activate the pump to provide irrigation fluid to be transferred to the user through the probe. This may be controlled by a control button 44, as in the illustrative example. Irrigation will, as discussed above, preferably immediately be aborted once the button 44 is released. A further control button 43 may be provided for reverse operation, e.g., to empty the tubes and the probe from irrigation fluid once irrigation has been completed, and/or to release overpressure from the irrigation liquid reservoir. This control element is preferably also provided with a dead man's handle functionality. Alternatively, a single control element with several operation states, such as a rocker lever, may be used here as well.

The arrangement of separate control elements for controlling the balloon on the one hand, and the irrigation on the other, presents several advantages. For example, the control unit becomes simpler and less costly to produce. Further, the operation becomes more transparent and controllable for the user.

It is possible to make the control elements for the balloon and the irrigation, respectively, to be operable only one at a time, i.e. to lock the other control elements when one is used. However, preferably the control elements for the balloon and irrigation, respectively, are operable simultaneously. This makes it possible for the user to adjust the balloon filling, by inflation or deflation, during irrigation.

Figure 6:
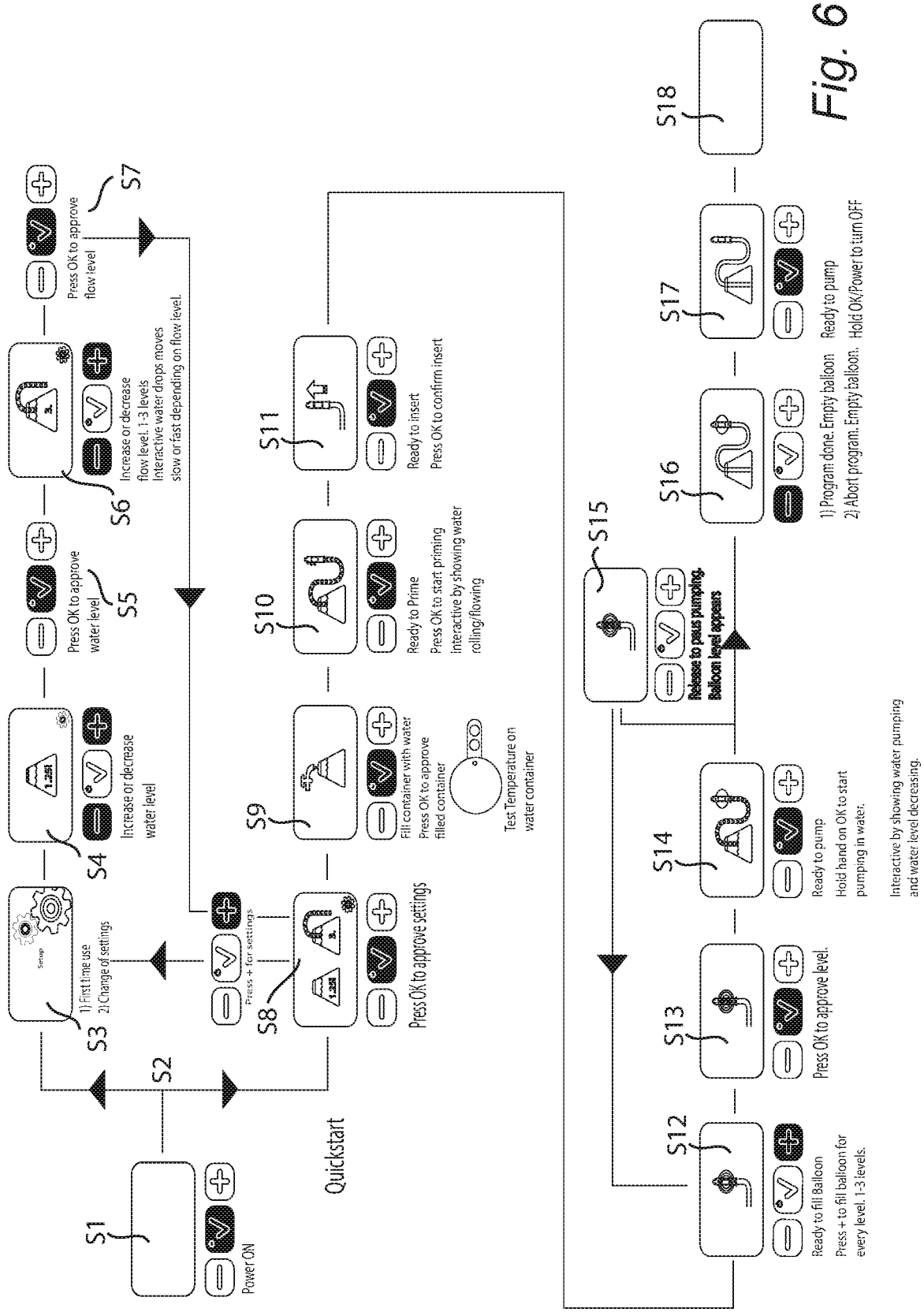
FIG. 6 is a schematic overview of the steps of an irrigation procedure using an irrigation system in accordance with the disclosed technology.

By use of the certain embodiments in accordance with the disclosed technology, anal irrigation can be carried out by a sequence of steps, which will now be discussed with reference to the schematic illustration of possible display showings, as illustrated in FIG. 6.

Here, three control buttons are used: one marked as "−", indicating a decrease, one marked "+", indicating an increase, and one marked "√", indicating a confirmation, OK. These buttons will be referred to in the following as "decrease", "increase" and "confirm", respectively.

In a first step S1, the control unit is activated, and a choice is made, S2, whether to enter an initiation scheme, or to quick-start the irrigation procedure. If this is the first time the irrigation system is used by the user, the initiation scheme is preferably required, whereas for a restart or a reuse of the irrigation system the quick-start path may be chosen. However, the initiation scheme may be used even after the first time, to alter the settings and the like.

In the initiation scheme, a display is first shown, S3, that a parameter setting mode is entered. In a following step, S4, the volume of irrigation liquid to be used for the irrigation is determined. The desired volume is set with the increase and decrease buttons. In a following step, S5, the set volume is accepted by pressing the confirm button. However, this step may also be omitted, in which case the process proceeds immediately to the next step. In a following step, S6, the desired flow rate is determined. Again this is done with increase and decrease. The flow rate is preferably selectable among a predetermined number of pre-selected fluid rates. For example, three, four, five or more different flow rate levels may be provided. In a subsequent step, S7, the selected level is confirmed.

The settings for the user are preferably stored, and are reused in the next irrigation. The parameter settings may, e.g., comprise one or several of: total irrigation liquid volume, flow rate for the irrigation liquid and fluid volume for inflating the inflatable retention member. It is also possible to store several parameter settings, or even storing of the parameter settings for every irrigation process being conducted, and to select and retrieve any of these stored parameter settings for reuse.

The user is then asked whether the determined settings are accepted in step S8. Pressing of confirm at this stage brings the user forward to the next stage, whereas a negative confirmation, e.g., by pressing increase, brings the user back to the setting stage, step S3. However, step S8 may also be omitted, and the process may immediately go from step S1 to step S9. In this case, the parameter setting process may be reached by activating a separate "setting" button, or by any other means useable to change mode.

Having completed the initiation, the user is requested, in step S9, to fill up the reservoir with liquid, such as water. When this is done, confirm is pressed to confirm completion of this step. However, confirmation is optional, and may be omitted. In this case, the process will proceed to the next step immediately, without requesting confirmation. Optionally, a temperature check of the filled liquid can be done at this stage, and an alarm may be provided to the user if the temperature is too high or too low.

In a following step, S10, the user is asked to confirm that priming of the system should be made. Priming may, e.g., comprise pumping of irrigation to fill the tubing with liquid, etc. At this stage, the probe may remain in its package. If the probe is provided with a hydrophilic coating, irrigation liquid may also be pumped to ensure that the hydrophilic coating is properly wetted and activated. However, the confirmation may again be omitted, in which case the priming step is performed without request for a confirmation. Further, for some applications the entire priming step may be omitted.

When priming is completed, the user is asked, in step S11, to insert the probe in the operational position. When this has been done, this is confirmed by pressing confirm. The user is then asked to confirm that he/she is ready for filling of the balloon. However, both said confirmation steps may be omitted, in which case the process immediately proceeds to the next step, without requesting confirmation. Filling of the balloon is preferably made to one of a few predetermined filling levels. Here, in step S13, pressing of the increase button once fills the balloon to the first, lowest filling level. Pressing of the increase button once again fills the balloon to the second filling level. Pressing once again fills the balloon to the highest filling level. However, alternative ways of filling the balloon are feasible. For example, more or fewer predetermined filling levels may be used. For example, only one level, as set in the parameter setting mode, may be used, whereby filling this level will be performed automatically until this level is reached, or until the filling is aborted. Further, the filling may be performed continuously while the increase button is depressed. Further, deflation of the balloon may be obtained by pressing the decrease button. Further, the balloon may be alternatively be made by means of a separate, and preferably hand-operated, pump, as has been discussed in the foregoing. If so, the user may simply be requested to confirm that an appropriate filling level has been achieved. However, for many other filling methods, no explicit confirmation would be needed.

In a further step, S14, the user is requested to confirm that he/she is now ready for irrigation. In this stage, continuous depression of the confirmation button is requested. The progress of the irrigation may be indicated on the display, as a progress bar, indication of volume that has been pumped or is remaining, time left, etc. If it is determined, step S15, that the confirmation button has been released prior to completion of the irrigation, the process is brought back to step S12 as a safety measure. Hereby, the activation of the pump functions as a "dead man's handle", so that irrigation will immediately be aborted if something unintentional occurs.

If the irrigation process is not aborted, the irrigation continues until the predetermined volume of irrigation liquid has been discharged. When irrigation has been completed, step S16, the user is asked to deflate the balloon by pressing decrease. When this has been done, and the probe has been removed, the user is asked to dry the system, step S17, by pressing confirm, whereby remaining irrigation liquid in the tubing is pumped out. Then, the control unit may be powered off, and the irrigation is completed, step S18.

The above-discussed irrigation process can naturally be varied in many ways, as would be apparent for the skilled addressee. For example, several of the steps may be omitted, combined or executed in a different order. For example, several of the confirmation steps may be omitted, so that the procedure can perform several of the steps automatically, without requesting confirmation from the user. The initiation/parameter setting stage may also be omitted in the default procedure, and instead being separately accessible upon request. This is, e.g., of advantage in applications were parameter settings are to be made primarily by a physician or the like, and where the user is normally not intended to alter the parameter settings. However, additional steps of confirmation, parameter setting and the like may also be added to the process.

As a further illustration of the variations in procedural steps which are feasible, another embodiment illustrating a process involving fewer steps is will now be discussed with reference to FIG. 7. In order to simplify understanding, the same or similar steps as discussed above in relation to FIG. 6 are assigned the same or similar reference denominations.

In a first step S1, the control unit is activated.

Following activation, the process immediately proceeds to a priming step S10'. Priming may, e.g., comprise pumping of irrigation to fill the tubing with liquid, etc. At this stage, the probe may remain in its package. If the probe is provided with a hydrophilic coating, irrigation liquid may also be pumped to ensure that the hydrophilic coating is properly wetted and activated. As in the previous embodiment, the confirmation step may be omitted.

When priming is completed, the user is asked, in step S11, to insert the probe in the operational position. When this has been done, this is confirmed by pressing confirm. As in the previous embodiment, the confirmation step may be omitted.

Next to follow is a balloon inflation/deflation step S12'. This step may be identical to the balloon inflation/deflation described previously in relation to FIG. 6. However, preferably step S12' does not operate with predetermined filling levels. Instead, the balloon is continuously inflated when the increase button is depressed. Further, filling of the balloon is preferably immediately aborted as soon as the button ceases to be depressed. Similarly, the balloon is continuously deflated when the increase button is depressed. Further, deflation of the balloon is preferably immediately aborted as soon as the button ceases to be depressed. Hereby, the user can easily inflate the balloon to a desired level by keeping the increase button depressed until a desired filling level has been obtained, and thereafter release the button. The filling level may then be fine adjusted by short term depression of the increase and decrease buttons, thereby to adjust the filling level upwards or downwards, respectively. When a satisfactory balloon filling level has been obtained, this is confirmed by activating the confirm button. This also confirms that the user is now ready for irrigation. As in the previous embodiment, the confirmation step may be omitted.

In this step S14', depression of the confirmation button, or alternatively the increase button, activates pumping of the irrigation liquid through the catheter. The progress of the irrigation may be indicated on the display, as a progress bar, indication of volume that has been pumped or is remaining, time left, etc. Pumping continues as long as the button continues to be depressed. However, as soon as the button is released, pumping is immediately aborted, in analogy to what has been discussed previously. Hereby, the activation of the pump functions as a "dead man's handle", so that irrigation will immediately be aborted if something unintentional occurs. Pumping may also optionally be automatically aborted, despite depression of the button, if it is determined that the reservoir holding the irrigation liquid has been emptied. Pumping may also optionally be automatically aborted, despite depression of the button, when it is determined that a predetermined irrigation volume has been irrigated.

When pumping has been stopped or aborted, the process proceeds to step S15', in which the user is informed that pumping has been aborted, and/or the level of balloon inflation is presented. Other information may also be presented to the user in this step. Further, this step may also be omitted.

After a predetermined time, or after confirmation by the user, e.g., by depressing the confirm button, or alternatively immediately after abortion of pumping of the irrigation liquid (in case step S15' is omitted), the process returns to step S12'. Here, the user may re-adjust the filling level of the balloon, as described previously, by using the increase and decrease buttons. The user may also confirm that the balloon pressure is satisfactory, and again proceed to the irrigation step S14' by depressing the confirm button. However, if it is or has been determined that the reservoir holding the irrigation liquid has been emptied and/or that a predetermined irrigation volume has been irrigated, proceeding to step S14' may optionally be hindered.

In step S12', the balloon may further be deflated for withdrawal of the catheter, after completed irrigation or when a user wishes to abort the procedure prior to completeness. Deflation is accomplished by continuous depression of the decrease button. When the balloon has been deflated, the user confirms this by depression of the confirm button, and the process then ends in step S18.

The irrigation process may, however, be even further simplified. In a very simple process, the irrigation system is operated in the following way:

The irrigation system is turned on.

The irrigation system is operated to pump irrigation liquid through the probe for priming.

The probe is inserted in operative position in the user.

The inflatable retention member is inflated so that a predetermined filling level is achieved.

Irrigation liquid is pumped until a predetermined total volume has been pumped.

The inflatable retention member is deflated.

The process is ended.

Figure 7:
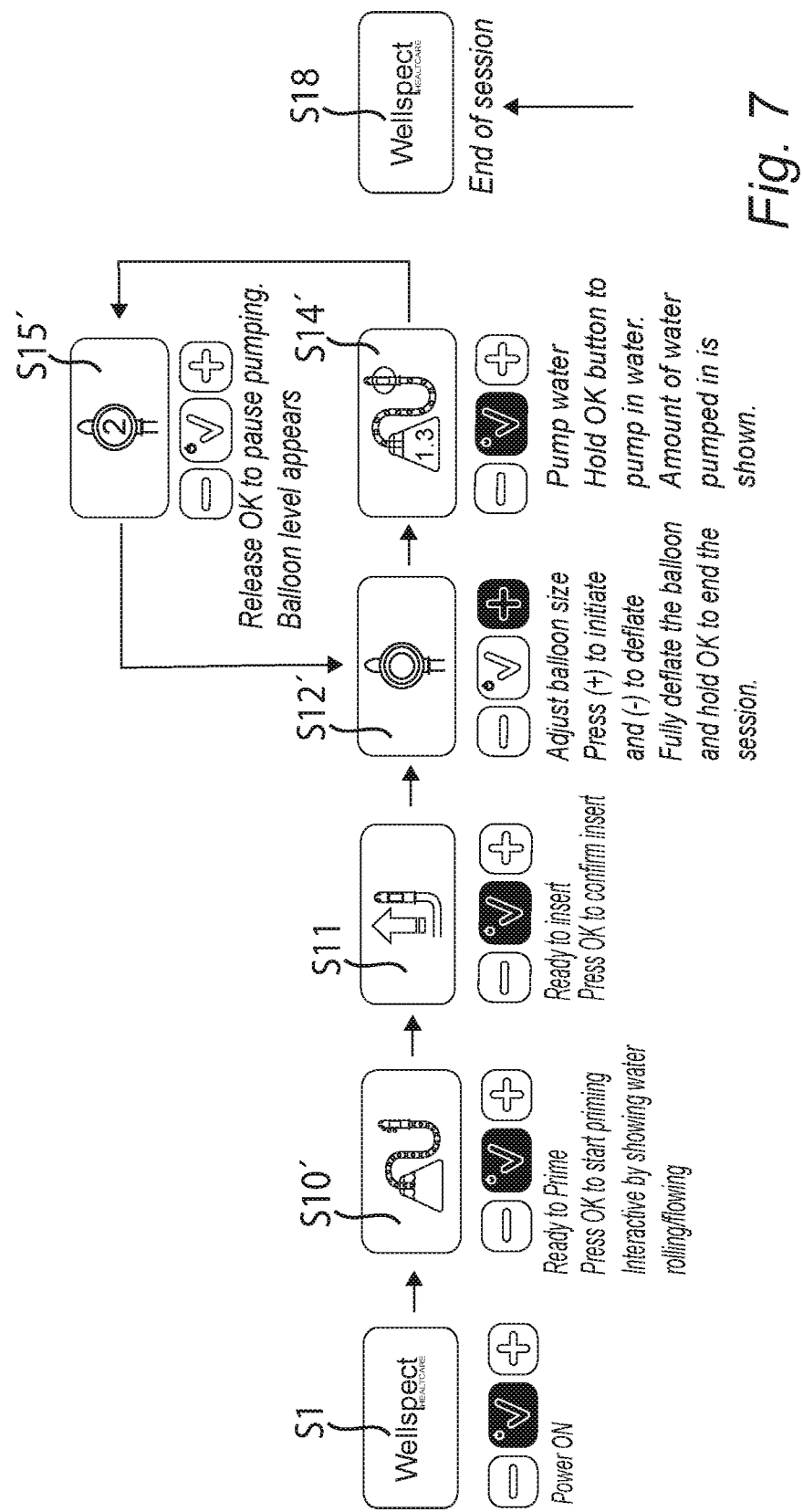
FIG. 7 is a schematic overview of the steps of an alternative embodiment of an irrigation procedure using an irrigation system in accordance with the disclosed technology.

Even in the simplified procedure discussed above, or the in the simplified procedure discussed in relation to FIG. 7, a parameter setting mode or the like may optionally be provided, e.g., to determine a predetermined irrigation volume to be used for irrigation, to adjust the, pumping speed for inflating/deflating the balloon and/or for pumping the irrigation liquid, etc. The parameter setting mode may be entered by simultaneous depression of two or more of the control buttons, by activation of a further control button, by connecting the control unit to an external device, or the like.

Thus a desired flow rate may be set and input by the user in various ways prior to irrigation, e.g., in a parameter setting mode as discussed above. However, the desired flow rate may also be input in other ways, such as via a remote control or the like.

Further, it is also possible to allow the desired flow rate to be adjusted during the irrigation procedure. For example, it is possible to use switches for pumping also sensing the pressure level being applied by the user to the control element, and to adapt, e.g., the desired flow rate value in accordance with the determined pressure level. For example during the irrigation step S14 or S14', it may be determined if the applied pressure to the confirm button is exceeding a certain threshold level, and if so use a higher flow rate value, and if not, to use a lower flow rate value. More than two low rate values may also be provided. Pumping may also optionally be automatically aborted, despite depression of the button, if it is determined that the reservoir holding the irrigation liquid has been emptied.

Further, the desired flow rate may be varied in direct correlation to the applied pressure.

Alternatively, the user may be given the opportunity of determining the desired flow rate directly by provision of two or more dedicated control buttons related to "increase", "decrease" and "confirm". The user may then select whether to use the high or low flow rate for a certain action, and may also use these buttons to adjust the desired flow rate during use.

Figure 8:
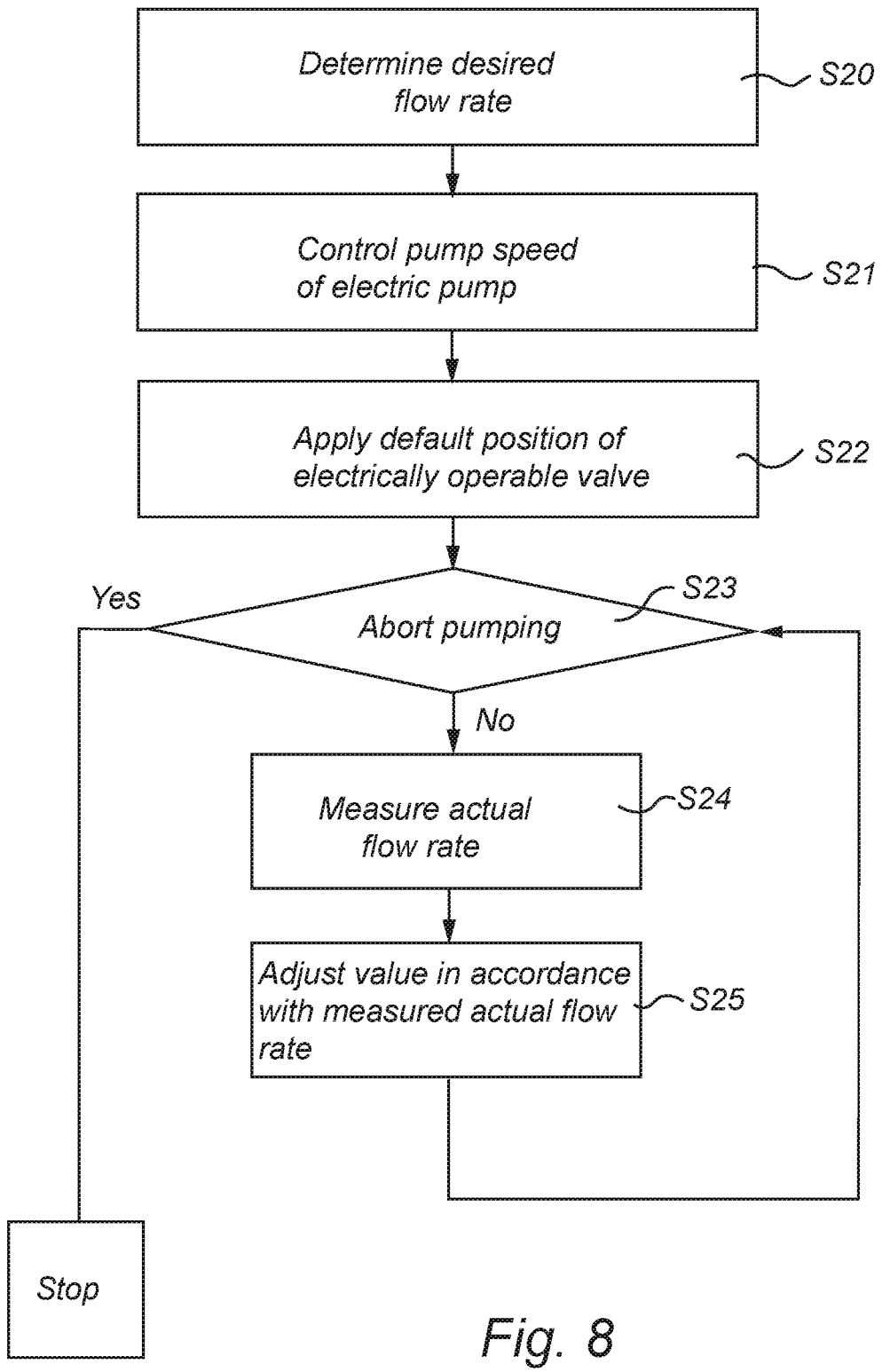
FIG. 8 is a schematic flow chart illustrating steps of flow rate control using an irrigation system in accordance with the disclosed technology.

An embodiment of the flow rate control will now be discussed in more detail, referring to FIG. 8. This control is preferably realized as a software control in the controller 31, 31', but may alternatively be realized partly or totally with hardware circuitry.

In a first step, S20, a desired flow rate is determined. The desired flow rate may, as discussed in the foregoing be decided and input by the user in various ways. Preferably, the user is given the opportunity to select between a number of predetermined flow rate levels, such as between 2-10 different flow rate levels, and preferably between 4-7 flow rate levels. For example, flow rates in the range of 25 ml/min-1500 ml/min can be provided, and preferably in the range 50 ml/min-1000 ml/min, and most preferably in the range 100 ml/min-750 ml/min. However, it is also possible to enable for the user to select freely within the provided range, without being bound to any specific predetermined values, e.g., by simply entering the exact value of the desired flow rate, or to use "+" and "−" buttons to increase/decrease a selected value.

Once a desired flow rate has been determined, the controller determines a pumping speed for the electric pump in step S21. The pumping speed of the electric pump may be controllable in a number of preset levels, such as between 2-10 different flow rate levels, and preferably between 4-7 flow rate levels. In this case, the controller selects one of the preset flow rate levels which are above the desired flow rate, but preferably still relatively close to this desired flow rate. For example, the controller may decide always to use the flow rate level of the pump which is closest to the desired flow rate, but still exceeding this. However, alternatively, the controller may also check whether this closest flow rate level is too close to the desired flow rate, such that the difference between this flow rate level and the desired flow rate level is below a predetermined threshold value, and then instead choose the second closest flow rate level for the pump. It is also possible, particularly if the electric pump is controllable to any flow rate level within a certain range, to select a flow rate level which is within a certain range from the desired flow rate, such as being 10%, 15% or 25% above the desired flow rate, being somewhere within the range 5-25% or 10-20% above the desired flow rate, being 10, 25 or 50 ml/min above the desired flow rate, being somewhere within the range 10-100 or 20-50 ml/min above the desired flow rate, or the like. Thus, a coarse first setting of the flow rate in accordance with the desired flow rate is made in this step S21.

In dependence on the rules used for selecting the pumping speed for the electric pump, a default setting of the electrically operable valve may be applied, in step S22. Hereby, the valve may, e.g., be controlled, as a default, to be 10%, 15% or 20% closed. However, this step is optional, and may also be omitted.

It is then determined, step S23, whether the irrigation process should be aborted, due to input from the user, such as release of the pumping control element. If not, the actual flow rate is determined by the flow sensor, step S24, and the measurement data is inputted to the controller.

The controller determines whether there is a need to increase or decrease the flow rate based on the received actual flow rate and the determined desired flow rate, and adjust the electrically operable valve in accordance with this, step S25, in accordance with any appropriate regulation scheme.

The process is then repeated from step S23, as long as the irrigation process is not aborted, and when the irrigation process is aborted, the control process is terminated.

In case adjustment of the desired flow is allowed to be adjusted not only before irrigation starts but also during irrigation, as discussed in the foregoing, the loop of the method may instead return to step S20 all the time, to renew the determination of the desired flow rate.

The person skilled in the art realizes that the present invention is not limited to the preferred embodiment or embodiments. For example many different types of hand-operated or powered pumps may be used. Further, the control elements may be realized in many different ways, such as mechanical control buttons, galvanically isolated touch buttons, areas on a touch screen and the like. The control elements may also, additionally or alternatively, be arranged on a remote control. Also, many types of electrically operable valve may be used for the flow rate control.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. An irrigation system for controlling fluid flow, comprising:
- a reservoir to hold an irrigating liquid;
- a probe able to be inserted in a user;
- tubing to provide fluid communication between said reservoir and said probe;
- an electrical pump to indirectly pump the irrigation liquid from the reservoir to the probe through said tubing, said electrical pump being controllable to assume a plurality of predetermined flow rates, wherein the plurality of predetermined flow rates is at least four;
- an electrically operable valve, arranged so that the irrigation liquid is transferred from the reservoir to the probe via the electrically operable valve, and arranged to continuously control a degree of openness of said tubing between a fully closed state and a fully opened state, and intermediate states therebetween;
- a flow sensor to measure an actual flow rate of the irrigation liquid in the probe; and
- a controller arranged to obtain a desired flow rate from a user interface, and configured to control the flow rate of the electrical pump to one of said plurality of predetermined flow rates exceeding said desired flow rate, wherein the controller is arranged to control the flow rate of the electrical pump to one of said plurality of predetermined flow rates exceeding said desired flow rate which is closest to the desired flow rate and to control the flow rate of the electrical pump to one of said plurality of predetermined flow rate exceeding said desired flow rate by less than 25%, and to continuously regulate the electrically operable valve based on the measured actual flow rate, thereby limiting the flow rate provided by the electrical pump to obtain said desired output flow rate, whereby a double control of the flow rate is provided, with a first, coarse control of the flow rate provided by controlling the electrical pump, and a second, finer control of the flow rate is provided by controlling a degree of openness of the electrically operable valve.

2. The irrigation system of claim 1, wherein the controller is arranged to control the flow rate of the electrical pump to one of said plurality of predetermined flow rate exceeding said desired flow rate by less than 15%.

3. The irrigation system of claim 1, wherein the controller is arranged to control the flow rate of the electrical pump to one of said plurality of predetermined flow rate exceeding said desired flow rate by less than 10%.

4. The irrigation system of claim 1, wherein the electrically operable valve is a clamping or pinch valve, providing a controllable clamping/pinching action on a tube leading between the electrical pump and the probe.

5. The irrigation system of claim 4, wherein the electrically operable valve comprises a movable arm that is connected to a constriction structure, said constriction structure being arranged opposite to an abutment, and with the tube extending between said constriction structure and said abutment, whereby movement of the moveable arm moves the constriction structure to control compression of the tube between said constriction structure and said abutment.

6. The irrigation system of claim 5, wherein the moveable arm is rotatable, and comprising a cam shape engaging said constriction structure.

7. The irrigation system of claim 1, wherein the probe is provided with an inflatable retention member.

8. The irrigation system of claim 7, further comprising a second pump to inflate the inflatable retention member.

9. The irrigation system of claim 1, further comprising a control unit with a housing, said housing enclosing said electrical pump, said electrically operable valve, said flow sensor and said controller.

10. The irrigation system of claim 9, wherein the tubing includes a first part connecting the control unit with the probe and a second part connecting the reservoir with the control unit, and wherein each of said first and second parts comprises a gas conducting tube and an irrigating liquid conducting tube.

11. The irrigation system of claim 1, wherein the electrical pump is controllable to assume a plurality of predetermined flow rates by control of a voltage supplied to the electrical pump.

12. The irrigation system of claim 1, wherein the system is a rectal irrigation system.

* * * * *